United States Patent [19]

Rusch

[11] Patent Number: 4,963,129
[45] Date of Patent: Oct. 16, 1990

[54] SYSTEM FOR THE DRAINAGE OF BODY CAVITIES

[75] Inventor: Heinz Rusch, Waiblingen, Fed. Rep. of Germany

[73] Assignee: Willy Ruesch AG, Fed. Rep. of Germany

[21] Appl. No.: 407,433

[22] Filed: Sep. 6, 1989

[30] Foreign Application Priority Data

Sep. 17, 1988 [DE] Fed. Rep. of Germany ....... 3831652

[51] Int. Cl.$^5$ .......................................... A61M 25/00
[52] U.S. Cl. ....................................... 604/8; 604/170; 604/283
[58] Field of Search ............................... 604/280–283, 604/8–10, 170, 171

[56] References Cited

U.S. PATENT DOCUMENTS

| 4,713,049 | 12/1987 | Carter | 604/8 |
| 4,820,262 | 4/1989 | Finney | 604/8 |
| 4,834,709 | 5/1989 | Banning et al. | 604/170 |

FOREIGN PATENT DOCUMENTS

| 2907832 | 2/1979 | Fed. Rep. of Germany . |
| 3339179 | 10/1983 | Fed. Rep. of Germany . |
| 8614013 | 5/1986 | Fed. Rep. of Germany . |
| 3714839 | 5/1987 | Fed. Rep. of Germany . |
| 8801101 | 1/1988 | Fed. Rep. of Germany . |

Primary Examiner—John D. Yasko
Attorney, Agent, or Firm—Griffin Branigan & Butler

[57] ABSTRACT

Prior-art systems for drainage of body cavities, in particular renal cavity systems, have usually consisted of a flexible drainage tube (1) with at least one crooked end (11, 13), a tubular device, called a pusher (2), serving to push the drainage tube (1) into a body cavity, a distal end of which is connected in a separable way with a proximal end of the drainage tube (1), and a guide wire (3) passing through the drainage tube (1) and the pusher (2). Up to now, the separable connection consisted of either a predetermined break point or a wedge connection. Both solutions have been unsatisfactory.

According to this invention, ends of a drainage tube (1) and a pusher (2), which are connected with each other, have parts (41, 42) of a lock (4) complementary to each other, which define sections (45, 46) overlapping each other and featuring facing sections fitted to each other which transmit axial traction forces and a torque. Sections (45, 46) are held in mesh by the guide wire (3) passing through them. Thereby, each part (41, 42) of the lock (4) has, at a spaced distance from its end, a transverse slot (43, 44), with the section (45, 46) defining or delimiting the transverse slot (43, 44) presenting on its periphery a flattening (47, 48) parallel to a slot base.

9 Claims, 3 Drawing Sheets

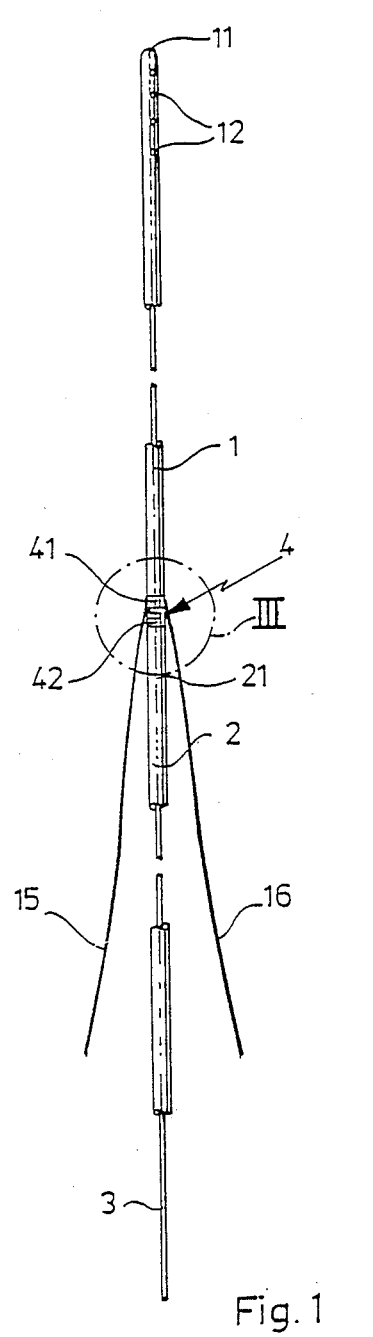
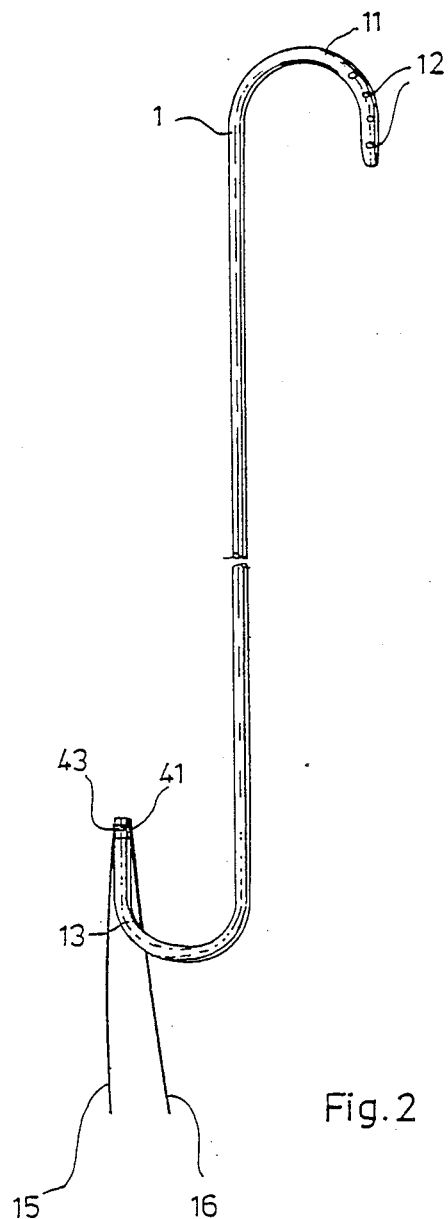
Fig. 1
Fig. 2

SYSTEM FOR THE DRAINAGE OF BODY CAVITIES

BACKGROUND OF THE INVENTION

This invention relates to a system for the drainage of body cavities, in particular renal cavity systems, and consists of a flexible drainage tube with at least one crooked end, a tubular device, or pusher, designed to push forwardly the drainage tube into the body cavity, a distal end of which is connected in a separable manner with a proximal end of the drainage tube, and a guide wire passing through the drainage tube and the Pusher.

Such systems are known in various forms of construction. Such a drainage tube serves to hold open narrowed, natural or artificial, body channels and to ensure transport of body fluids from one hollow organ to another or, as well, from hollow organs or layers of tissue to outside. The pusher and the guide wire serve to insert the drainage tube into the body channel to be held open.

A particular field of application is the drainage of renal cavity systems. In this context, it is necessary to insert such a drainage tube into a ureter which connects the renal pelvis and urinary bladder. To that end, a drainage tube which is, at least at one end, but preferably at both ends, crooked like a "J" or even rolled like a "pigtail" has proven to be particularly successful. Drainage tubes crooked at both ends are also known under the designation "Double J" or "Pigtail". The guide wire serves in this connection to extend the crooked ends of the drainage tube. Such a system is produced and marketed by the inventor's assignee under the designation "Integral-Uretersplint-Set", see for instance Willy Rüsch AG's catalogue from 1986 "Urologie II/6".

The purpose of the crooked ends of the drainage tube is to anchor the drainage tube through its ends in the renal pelvis and in the urinary bladder, respectively, and to prevent thereby the drainage tube from drifting in the ureter. It can be easily seen that introduction of the drainage tube not only requires the axial shifting thereof, but, if necessary, also rotation thereof, in order to bring the crooked ends into the hollow organs in correct positions for faultless fit. In this context, forces required for shifting and rotating the drainage tube are transmitted by the Pusher which, for this purpose, is firmly connected with the drainage tube.

After insertion of the drainage tube, the guide wire and the pusher must be removed. While the guide wire may simply be pulled out of the drainage tube and the tube-like pusher, the connection between the drainage tube and the pusher has to be interrupted. Known systems present a firm connection between a pusher and the drainage tube, which has to be interrupted by means of a special device. Carrying out such an interruption is extremely difficult, since a separating device has to be inserted either through a cystoscope used for insertion of the drainage tube or else directly through the ureter. In another known system, a pusher is wedged mechanically with a drainage tube; however, such a system is also unsatisfactory because the wedge connection may prematurely loosen uncontrollably during insertion of the drainage tube, or become so fixed that a later separation is no longer possible without difficulties.

Therefore, an object of the invention is to connect, within a system described above, a pusher with a drainage tube in such a manner that faultless transmission of forces required for placing of the drainage tube is ensured, while, however, the connection between the drainage tube and the pusher remains easily separable.

The problem is solved, according to the invention, in the following way: Connected ends of drainage tube and the pusher are equipped with complementary parts of a lock which present mutually overlapping sections; the latter have face sections fitted onto each other, being suitable for the transmission of axial traction forces as well as torque, and being held meshed by means of a guide wire passing through, or permeating, them.

With a system according to the invention a perfect, form-fitted interlocking connection between the pusher and the drainage tube is created by means of a lock, the parts of which are locked by the guide wire. This connection provides an unimpeded transmission of all axial forces and torques from the pusher to the drainage tube. The said connection is, however, undone as soon as the guide wire has been pulled out, since then the two parts of the lock are no longer held together but tend to separate by themselves because the end of the drainage tube connected with the end of the pusher, which so far had been extended by the guide wire, now moves to return its crooked position and thereby separates from the end of the pusher. Therefore, it is advantageous if the faces ensuring the power transmission are arranged on an outer face of the crooked end of the drainage tube.

In a preferred embodiment of the invention, each part of the lock presents at a spaced distance from its end a transverse slot and a section delimiting, or defining, the transverse slot has on its periphery a flattening parallel to a base of the slot. In this system, each part receives in its transverse slot the section of the other part delimitating the transverse slot, and the section delimiting the transverse slot of one part is fitted with its flattening onto the base of the slot of the other part, respectively. The sections meshing with the transverse slots of the other parts, their faces being laid at right angles to an axis of the drainage tube and the pusher, ensure a faultless transmission of axial traction forces, whereas a form-closed interlocking fit between the parallel flattenings of the sections delimiting the transverse slot and the, respectively, adjacent slot base also guarantee a faultless transmission of torques. In this respect, it is particularly advantageous for holding the parts of the lock perfectly together, if the transverse slot intersects with the bore of the part, since in that case the section delimiting the transverse slot also presents a closed bore through which that section is perfectly centered with the guide wire.

The parts of the lock may be formed by certain parts which are fitted into the drainage tube and/or the pusher, but they may also be formed directly as part of the drainage tube and/or the pusher. If fitted parts are used, they may consist of any sufficiently firm, medically safe material, preferably of metal or plastic.

In a further embodiment of the invention, the lock is supported by a sleeve.

This has the advantage that a drainage tube connected with a pusher can be threaded coaxially on an already set spiral mandrel. For that purpose, a tip of the drainage tube features a perforation through which the drainage tube can be threaded onto the spiral mandrel. As soon as the spiral mandrel has pierced bore openings of the lock, the sleeve can be removed. The lock is held together in a centered manner by the spiral mandrel.

In still another embodiment of the invention, a sleeve can be snapped open in two halves.

This has the advantage that complementary parts of the lock can be firmly pressed together and that the sleeve has an axially immovable fit at the end of the pusher and the drainage tube. As soon as the spiral mandrel holds together the parts of the lock, the sleeve may be taken off the ends of the drainage tube and the pusher simply by snapping open the halves of the sleeve.

After termination of the described drainage, the drainage tube has to be removed again from the body cavities. This removal is obtained through known methods, in particular through an endoscopical intervention. If the drainage tube is to remain only for a short time, it has proven successful to fix thin threads to the drainage tube which hang out of the body channel, for instance the ureter, so that removal of the drainage tube may be obtained by pulling ends of the thread. In a system according to the invention, it is possible to attach at least one thread to the lock part of the drainage tube which is so long that, the drainage tube being in place, it protrudes from the body cavity and thereby allows the drainage tube to be pulled out.

In the following, the invention is described and explained in more detail by means of embodiments of the invention as presented in the drawings. The characteristics as they appear from the description and the drawings can be applied individually or in any combination in other embodiments of the invention.

BRIEF DESCRIPTION OF THE DRAWINGS

It is shown in

FIG. 1: a side elevation of a system according to the invention for drainage of body cavities;

FIG. 2: a side elevation of the drainage tube of the system as shown in FIG. 1, a guide wire having been pulled out and a pusher having been separated;

The system as shown in FIG. 1 comprises a drainage tube 1, a pusher 2 and a guide wire 3 passing through, or permeating, the drainage tube 1 and the pusher 2. The drainage tube 1 and the pusher 2 comprise a flexible tube, which can be manufactured, for instance, from a physiologically well tolerated plastic material. The drainage tube 1 is closed at is distal end 11, a tip of this catheter being preferable equipped in this area with drainage openings 12 perforating its walls. The drainage openings 12 can be grouped along the entire length of the drainage tube 1. In FIG. 2, the drainage openings 12 are shown only in the area of end 11. Further, the tip of end 11 of drainage tube 1 may present a perforation through which the drainage tube 1 can be threaded coaxially on an already set spiral mandrel. At its proximal end 13, i.e. the end pointing away from the catheter tip, the drainage tube 1 features a part 41 of a lock 4 which cooperates with another, complementary part 42 which is fitted onto a distal end 21 of the pusher 2, i.e. the end facing the drainage tube 1. The guide wire 3, inserted into the pusher 2 and the drainage tube 1, provides for stiffness of the system which is necessary for inserting the drainage tube 1 into a body cavity.

Figure 3:
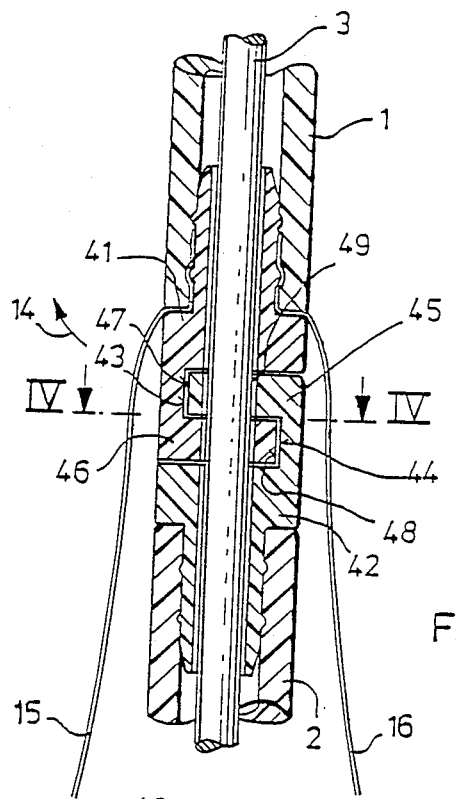
FIG. 3: a longitudinal section through section III of the system as shown in FIG. 1, on an enlarged scale.

The described embodiment deals with a drainage tube for connection of a renal pelvis with a urinary bladder, which is to be inserted into a ureter. The insertion is effected in the known manner, by means of a cystoscope. In this context, the drainage tube 1 is pushed forward by means of the pusher 2 protruding from the cystoscope, until it has reached a desired position.

The pusher 2, firmly connected with the drainage tube 1 by means of the lock 4, also offers the possibility of slightly withdrawings again the drainage tube 1 as well as of turning it, if necessary, in order to bring it into a correct position. Once the drainage tube 1 has been brought into the desired position, pusher 2 and guide wire 3 must be removed. The guide wire 3 may be pulled out from the pusher 2 and the drainage tube 1 without difficulty. Once the guide wire 3 has been removed, the lock 4 is undone so that also pusher 2 can be removed whereas drainage tube 1 remains in place. The ends 11 and 13 of the drainage tube 1 are pre-stressed so that they become crooked and form a kind of double J. Therefore, such drainage tubes are often also called "Double-J". The hook-like bends at the ends of the drainage tube 1 are useful for securing the latter against migrating in the ureter.

Figure 4:
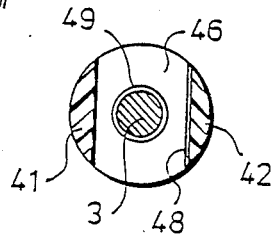
FIG. 4: a section, taken on line IV—IV through the system shown in FIG. 3.

As appears more clearly from FIGS. 3 and 4, parts 41 and 42 of the lock are fitted, respectively, into the ends of the drainage tube 1 or of the pusher 2. They may consist of metal, but also of plastic. Each of these parts has, spaced a distance from its end, a transverse slot 43, respectively 44, which is in mesh with a section 45, respectively 46, delimiting or defining the transverse slot of the other part. Each of these sections presents a flattening 47, respectively 48, which runs parallel to a slot base and by which each section is fitted to the slot base of the other part, respectively. The transverse slots 43, 44 are so deep that they intersect with a bore 49 of the part concerned, to the effect that the sections 45, 46 of parts 41, 42, delimiting the transverse slots 43, 44, also feature a bore 49 for the guide wire 3.

If the two complementary parts 41, 42 of the lock 4 are engaged, and permeated by the guide wire 3, they are form-fitted interlocked. The faces of the transverse slots 43, 44 and of the sections 45, 46 delimiting the transverse slots, which faces are oriented at right angles to the axis, allow for the transmission of axial traction forces, whereas flattenings 47, 48 of the sections 45, 46 meshing with the transverse slots, are fitted to the slot bases, allowing for the transmission of torques. If, however, after insertion of the drainage tube 1, the guide wire 3 is pulled out from the system, the form-fitted interlocking connection between the two parts 41, 42 of the lock 4 becomes easily separable. The transverse slot 43 in the part 41 fitted into the drainage tube 1 is oriented inversely to movement as shown by arrow 14, which movement the end 13 of drainage tube 1 tends to execute, in order to reach the crooked position shown in FIG. 2. This means that the transverse slot 43 in the part 41 is oriented towards the outer face of the crooked end of the drainage tube 1. Inasmuch as a certain friction between the parts 41, 42 interferes with this movement, such friction can be removed by slightly rotating the pusher 2 around its axis.

Figure 5:
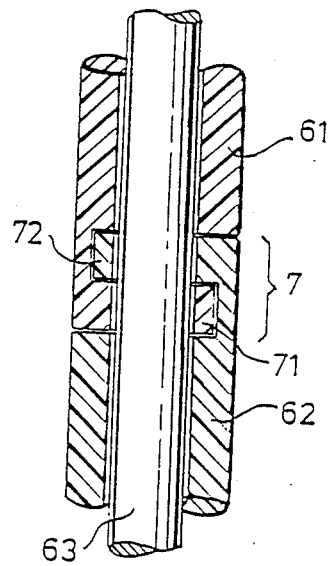
FIG. 5: a section, similar to FIG. 3, through another embodiment of the invention.

FIG. 5 shows an alternative embodiment of the invention, where a lock 7 presents the afore-mentioned configuration, but its parts 71, 72 are formed directly at respective ends of a drainage tube 61 and a pusher 62. Here, too, the parts 71, 72 are form-fitted together in the afore-mentioned way, as long as the guide wire 63 permeates the sections of the drainage tube 61 and the pusher 62 which form the lock 7.

The removal of the drainage tube is usually effected through an endoscopical intervention. If, however, the presumed length of stay of the drainage tube is only a short one, in particular not more that five days, it is allowable to fix thin threads at the end of the drainage tube which are so long that they hang out from a body, i.e. in particular from a ureter. In this case, an endoscopical intervention can be avoided and the drainage tube can be pulled out simply by means of the threads. In the embodiment of the invention as shown in FIGS. 1 to 4, such threads 15, 16 are fixed, together with the part 41 of the lock 4, at the drainage tube 1.

It is clear that the invention is not limited to the above-described embodiments, but that modifications are possible without leaving the scope of the invention. In particular, a lock, connecting a drainage tube and a pusher according to the invention can be fixed at any drainage tube, whatever its form, e.g. in particular also to such catheter tubes which present only one crooked end, or where a bend is formed in a different way, as, for instance, in the case of drainage tubes called "Pigtail". Furthermore, the invention is not limited to special configurations of the complementary parts of the lock; the parts may, for instance, also present levelled faces which fit to each other and allow for the transmissions of axial and/or radial forces, as long as they are held together by a rod, but which, however, ensure a slight separation if the rod is removed. In this connection, it is not necessary to use as a rod a guide wire, which is needed anyway, but one can also imagine systems under which a wire to be pulled out from the outside is provided exclusively for the purpose of bolting together the parts of the lock.

Figure 6:
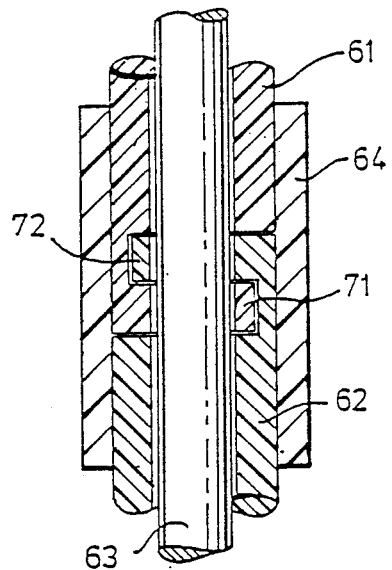
FIG. 6: a longitudinal section through a lock of this invention including a sleeve of this invention.

If the drainage tube 1 as shown in FIG. 6 is threaded coaxially on an already set spiral mandrel, the drainage tube 1 presents at its tip, the end 11, a perforation. As long as the spiral mandrel does not yet hold together the parts of the lock, the drainage tube 1 and the pusher 2 are held together by a sleeve 64, which either is a tubular sleeve slipped, before connecting the parts of the lock, over the end of the pusher 2 equipped with part of the lock and shifted, after connecting the parts of the lock, over the parts of the lock, or else is a sleeve which can be snapped open in two halves.

Figure 7:
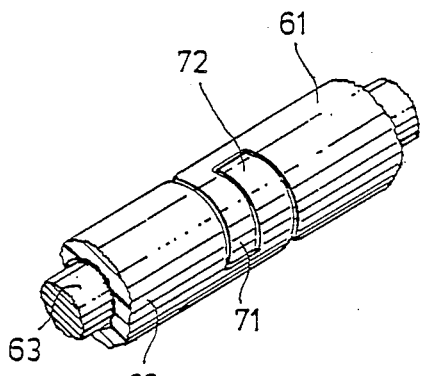
FIG. 7: a perspective view of a section of a lock according to the invention.

FIG. 7 shows in perspective view a section of the ends of the drainage tube 61 and the pusher 62. The presentation is not in real scale. The figure shows how the parts 71, 72 are meshed with each other form-fitted and interlocking and how the guide wire 63 holds together the parts 71, 72.

I claim:

1. System for the drainage of body cavities, in particular the renal cavity system, consisting of a flexible drainage tube with at least one crooked end, a tubular device, called pusher, serving to push the drainage tube into a body cavity, a distal end of which is connected in a separable manner with a proximal end of the drainage tube, and a guide wire permeating the drainage tube and the pusher, wherein the ends of the drainage tube (1) and the pusher (2), which are connected with each other, have parts (41, 42) of a lock (4), which are complementary to each other, and which feature sections (45, 46) overlapping each other, which sections (45, 46) are equipped with face sections adjacent to each other and suitable for the transmission of axial traction forces and a torque, and are held in mesh by the guide wire (3) permeating them.

2. System according to claim 1, wherein the faces serving for force transmission are arranged to the outside of the crooked end (13) of the drainage tube (1).

3. System according to claim 1, wherein each part (41, 42) of the lock (4) presents at a spaced distance from its end a transverse slot (43, 44) and the section (45, 46) delimiting the transverse slot (45, 46) presents on its periphery a flattening (47, 48) parallel to the slot base.

4. System according to claim 3, wherein the transverse slot (43, 44) intersects with a bore (49) of the part (41, 42).

5. System according to claim 1, wherein at least one part (41, 42) of the lock (4) is fitted into the drainage tube (1) and/or the Pusher (2).

6. System according to claim 1, wherein at least one part of the lock (7) is built directly into the drainage tube (61) and/or the Pusher (62).

7. System according to claim 1, wherein at least one thread (15, 16) is fixed at the drainage tube's (1) part (41) of the lock (4), which is so long that, when the drainage tube (1) has been inserted into a body cavity, it protrudes from the body cavity.

8. System according to claim 1, wherein the lock (4; 7) is supported by a sleeve (64).

9. System according to claim 8, wherein the sleeve (64) can be snapped open in two halves.

* * * * *